United States Patent
Henick-Kling et al.

(10) Patent No.: US 6,284,518 B1
(45) Date of Patent: Sep. 4, 2001

(54) SYNTHETIC MEDIA FOR THE PRODUCTION OF MALOLACTIC STARTER CULTURES

(75) Inventors: Thomas Henick-Kling, Geneva, NY (US); Sibylle Krieger, Ditzingen (DE)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 08/392,615

(22) Filed: Feb. 22, 1995

Related U.S. Application Data

(63) Continuation of application No. 08/273,772, filed on Jul. 12, 1994, now abandoned, which is a continuation of application No. 08/145,045, filed on Nov. 3, 1993, now abandoned, which is a continuation of application No. 08/008,879, filed on Jan. 25, 1993, now abandoned, which is a continuation of application No. 07/879,453, filed on May 4, 1992, now abandoned, which is a continuation of application No. 07/594,509, filed on Oct. 9, 1990, now abandoned.

(51) Int. Cl.$^7$ ...................................................... C12N 1/20
(52) U.S. Cl. ..................................... 435/253.6; 435/252.9; 426/12; 426/13; 426/14; 426/15
(58) Field of Search ............................... 435/253.6, 252.9; 426/12, 13, 14, 15

(56) References Cited

PUBLICATIONS

Henick–Kling et al., "Inhibition of Bacterial Growth and Malolactic Fermentation in Urine by Bacteriophage", *J. of Applied Bacteriology*, 61, pp. 287–293 1986.*

Beelman, R. B., et al, Dev. Ind. Microbiol. 23, 107–121 (1982).

* cited by examiner

*Primary Examiner*—Leon B. Lankford, Jr.

(57) ABSTRACT

This invention relates to the production of *Leuconostoc oenos* or Lactobacillus spp., preferably *Lactobacillus plantarum, Lactobacillus hilgardii, Lactobacillus brevis* or *Lactobacillus casei* biomass in novel synthetic media (which are free of fruit or vegetable or other natural juices). A key feature of the invention is the use of a fructose/glucose mixture where fructose is the primary carbohydrate source, as opposed to the more typical use of glucose or lactose. Fructose/glucose mixtures containing between 3% to about 45% glucose can be employed, preferably the amount is between about 5% and about 40% glucose. Most preferably, the amount of glucose is less then 20% of the mixture.

18 Claims, 4 Drawing Sheets

SYNTHETIC MEDIA FOR THE PRODUCTION OF MALOLACTIC STARTER CULTURES

This application is a continuation of application Ser. No. 08/273,772, filed on Jul. 12, 1994, now abandoned, which, is a continuation of application Ser. No. 08/145,045, filed on Nov. 3, 1993, now abandoned, which is a continuation of application Ser. No. 08/008,879, filed on Jan. 25, 1993, now abandoned, which is a continuation of application Ser. No. 07/879,453, filed on May 4, 1992, now abandoned, which is a continuation of application Ser. No. 07/594,509, filed on Oct. 9, 1990, now abandoned.

BACKGROUND OF THE INVENTION

Lactic acid bacteria (LAB) are of considerable importance in winemaking. The so-called malolactic fermentation (MLF), the conversion of L-malic acid to L-lactic acid and $CO_2$ by certain strains of lactic acid bacteria contributes much to the final wine quality. The conversion of malic acid to lactic acid reduces the acidity of wine. This is desirable in wines from cool wine growing areas which tend to have high acid contents (Wibowo et al., 1985, Am. J. Enol. Vitic. 36:302–313; Henick-Kling, 1988, in "Modern Method of Plant Analysis" New Serial Vol. 6, Springer Verlag, Berlin, p. 276–316; Radler, 1966, Zentralbl. Bakteriol. Parasitenk. Intektionskr. Hyg. Abt 2. 120:237–287; Amerine and Kunkee, 1968, Ann. Rev. Microbiol. 22:323–358; Ribereau-Gayon and Peynaud, 1975, Traitè d'Oenolgie Tome 2, Dunod, Paris).

Typically, spontaneous MLF occurs in wines of pH above 3.4 and is much delayed and irregular in wines of pH below 3.4 where MLF is most desirable for deacidification. This is due to the strong inhibition of growth of LAB at low pH. Inoculation of such wines with a large number of viable bacteria avoids the necessary growth before MLF is carried out. With a suitably prepared starter culture such as obtained with the medium described here, a wine can be inoculated with a cell density of $5 \times 10^6$ and $5 \times 10^7$ viable bacteria/ml. This represents a stationary culture at maximum cell density in wine, very little or no further growth is necessary for complete conversion of the malic acid. This procedure of inoculating with stationary phase cultures also is effective in avoiding phage interference (Henick-Kling et al., J. Appl. Bacterial. 61:525–534; 1986). It has been shown that Leuconostoc oenos can be attacked by bacteriophage during growth in wine and infection and lysis inhibits MLF (Sozzi et al., Rev. Suisse Vitic. Arboric. Hortic. 14:17–23; 1982. Henick-Kling et al., J. Appl. Bacteriol. 61:287–293; 1986). Recent investigations into the presence of phages in L. oenos show that 50% of all strains isolated from wine contain temporary phages. This and previous demonstrations of the presence of phages in wine show that cultures of L. oenos are susceptible to phage-induced lysis during growth in wine. Inoculation with a high cell density allows to avoid necessary growth and possible phage interference. Further, inoculation with high cell density ($5 \times 10^6$ to $5 \times 10^7$ viable bacteria/ml) ensures dominance of the introduced culture over indigenous LAB such as undesirable strains of Pediococcus. Inoculation with a dominating, selected strain of LAB gives protection against undesirable strains of Pediococcus and Lactobacillus. Thus the winemaker can control which strain of bacteria carries out MLF and he can give the wine the desired flavor characteristic of the selected strain. Stationary cell cultures may also be used in a cell reactor system (Gestrelius et al., U.S. Pat. No. 4,380,552). Also, wines which did undergo MLF are considered to be biologically stable (Kunkee, 1974, in "The Yeasts" Vol. 3, Yeast Technology, ACS, Wash. D.C.).

In winemaking, traditionally, the development of the indigenous bacterial flora, which originates from grapes and winery equipment, has been stimulated by several means: the use of none or small amounts of $SO_2$, adjustment of the pH to 3.2 or higher, maintaining a temperature of 16–20° C., and extended contact with yeast lees. More recently, starter cultures composed of lactic acid bacteria have been used to induce MLF (King, 1986, Dev. Ind. Microbiol. 26:311–321; Mayer et al., 1983, Schweiz. S. Obstund Weinball. 119:197–200; 1984, ibid 120:191–193; Lafon-Lafourcade, 1983, in "Biotechnology", Vol. 5, Verlag Chemie, Weinheim p. 43–53; Champagne et al., 1989, Appl. Environ. Microbiol. 55:2488–2492).

There are three genera of lactic acid bacteria, that are generally associated with MLF. They are species of Lactobacillus, Pediococcus, and Leuconostoc oenos (Radler, 1966, supra; Kunkee, 1967, Adv. Appl. Microbiol. 9:235–279; Maret et al., 1977, Ann. Technol. Agricoles 26:235–273; 1979, ibid 28:41–55). Leuconostoc oenos is generally the most predominant genus during active MLF, since this species is highly tolerant to the high acidity and ethanol in wine (Maret et al., 1979, supra; Davis et al., 1986, Appl. Environ. Microbiol. 51:539–545).

Strains of Leuconostoc oenos are the preferred lactic acid bacteria to carry out malolactic fermentation (MLF) because of their tolerance to low pH and alcohol and because of their preferred flavors produced.

Selected strains of LAB for induction of MLF in wine may comprise strains of Leuconostoc oenos, Lactobacillus plantarum, Lactobacillus hilgardii, Lactobacillus brevis, and Lactobacillus casei. Other options of reducing the content of malic acid in wine by the yeasts Schizosaccharomyces pombe or Schizosaccharomyces maledivorans have not given satisfactory wine quality.

Various studies have been performed to select lactic acid bacteria strains which are highly tolerant to the low pH and the alcohol content of wine (Kunkee, 1967, supra; Kunkee et al., 1964, Am. J. Enol. Vitic. 15:178–183; Beelman et al., 1977, Am. J. Enol Vitic. 28:159–165; 1980, ibid 31:269–276; 1982, Dev. Ind. Microbiol. 23:107–121; Silver et al., 1981, Am. J. Enol Vitic. 32:64–72; Lafon-Lafourcade, 1983, supra; Sandine, 1979, Pfizer Cheese Monographs, Vol VI, Pfizer Inc., NY; Sandine et al., 1985, U.S. Pat. No. 4,547, 373; King 1985, U.S. Pat. No. 4,562,077; 1987, EPO 141 878 B1). Some strains highly active in wine at low pH have been patented (Sandine et al., 1985, U.S. Pat. No. 4,547,373; King, 1985, U.S. Pat. No. 4,562,077). Very few studies have been performed on the biomass production of malolactic starter cultures for use in wine (Champagne et al., 1989, Appl. Environ, Microbiol. 55:2488–2492; and Lebensm. -Wiss. u. -Technol. 22:376–381; Schneider et al., 1987, FEMS, Microbiology Reviews 46/3: P. P56 D7). Previously described media for the production of Leuconostoc oenos biomass are based on grape juice, apple juice, or pear juice (Davis et al., 1985, supra) which is generally diluted and supplemented with yeast extract and tomato juice, Tween 80 and peptone or a mixture of vitamins (Krieger, 1989, Optimierung des biologischen Saureabbaus in Wein mit Starterkylturen., Ph.D. Thesis, Universitat Hohenheim, FRG). Recently, Champagne et al. reported the production of Leuconostoc oenos in apple juice based media (1989, Appl. Environ. Microbiol. 55:2488–2492) as well as the production of Leuconostoc biomass under pH control.

DESCRIPTION OF THE INVENTION

Figure 1:
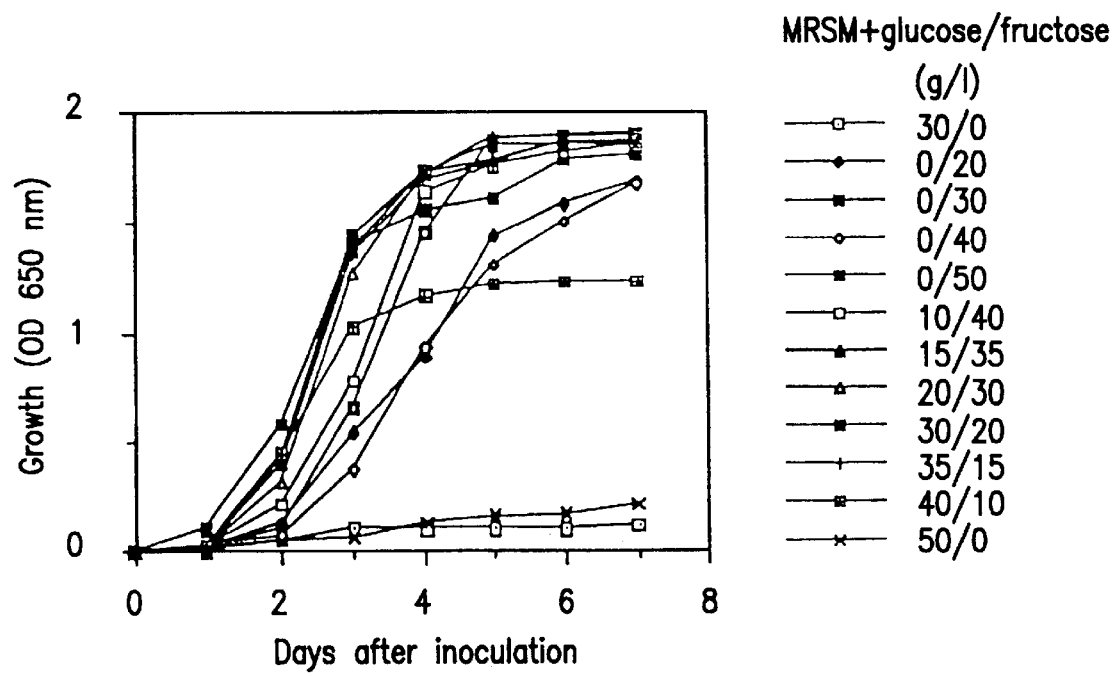
FIG. 1 shows growth of Leuconostoc oenos Lo107 in culture medium as a function of the glucose and fructose concentration in the medium.

This invention relates to the production of Leuconostoc oenos or Lactobacillus spp., preferably Lactobacillus plantarum, Lactobacillus hilgardii, Lactobacillus brevis or Lactobacillus casei biomass in novel synthetic media (which are free of fruit or vegetable or other natural juices). A key feature of the invention is the use of a fructose/glucose mixture where fructose is the primary carbohydrate source, as opposed to the more typical use of glucose or lactose. Fructose/glucose mixtures containing between 3% to about 45% glucose can be employed, preferably the amount is between about 5% and about 40% glucose. Most preferably, the amount of glucose is less then 20% of the mixture.

While commercially, relatively pure carbohydrate sources are preferred, one can employ high fructose corn syrups or other sources of fructose and glucose such as grape concentrates as the carbohydrate source, provided they contain appropriate ratios of fructose and glucose and do not contain inhibitory substances and further provided that the entire medium comprises the medium described herein.

The minimum amount of fructose containing carbohydrate mixture necessary in the media of the invention should be a biomass growth promoting amount, which for the preferred media described herein is at least about 0.5% of media. Typically about 4% is preferred. While amounts up to 6% or even more could be employed, but with little economic advantage.

For the purposes of description, the medium is described and quantified based upon an aqueous liquid medium. It is well understood in the art that the resulting starter culture can be provided, handled and/or employed as a liquid, frozen or lyophilized forms, as well as in an immobilized cell system, using techniques known in the art.

The amounts of nitrogen source in the media is at least that amount which is sufficient for desired biomass growth requirements, and are known to those skilled in the art. Malic acid and fructose containing carbohydrate components are used within limits which are not toxic to the desired biomass, but which are sufficient to cause a desirable growth rate. These amounts are easily determined by simple experiments. The ratio of malic acid to carbohydrate is preferably about 1 to about 20 parts of malic acid per part of carbohydrate.

The pH of the growth media is controlled through the use of buffers and/or, less preferably, the addition of appropriate acids or bases. The pH is chosen to maximize both growth rate and latter compatibility of the bacteria with the winemaking environment.

In the media of the invention, as biomass growth occurs, the pH is allowed to drop, but not typically below about 3.3. Preferably the pH chosen is a pH adapted for maximum growth of the culture, for example a range starting at about 6.5 to about 3.8, dropping as the biomass growth continues. For L. oenos typically the medium is inoculated at about pH 4.5 and drops to about 3.5 during biomass growth.

The use of fructose containing carbohydrate mixtures as described herein stimulates growth of L. oenos or Lactobacillus spp. and enhances their survival and malolactic activity in wine. The synthetic media allow rapid growth and high cell yield, for example when compared to media based on apple juice. In the white wine used in the Examples utilizing the preferred medium of the invention, the number of viable bacteria, two days after inoculation was up to 10 times higher for the bacteria cultured the synthetic medium containing 5 parts glucose and 45 parts fructose; and most importantly these cultures completed malolactic fermentation to 95% after 5 days while the other cultures with lower fructose content in the growth media only had degraded 15% of the malate. The higher malolactic activity of the culture prepared in the media of the invention with high fructose content (e.g. medium with, 5 g/l glucose 46 g/l fructose) was also evidenced in the test with the red wine which was not as inhibitory to the bacteria as was the white wine.

Aqueous synthetic media within the scope of the invention, suitable for growth of Leuconostoc oenos or Lactobacillus spp. biomass, in addition to containing the above-described carbohydrate source comprising fructose, must contain L. oenos growth supporting amounts of malic acid which stimulates the activity of transport and degradation in the malolactic fermentation process, i.e. a non-inhibitory malolactic fermentation ability enhancing amount of malic acid, as well as, in suitable well-recognized proportions, a suitable nitrogen source and essential minerals and vitamins. The term malic acid as used above includes suitable salts thereof, all in the L-form. DL mixtures may be used understanding that the active amount is the amount of the L-form present. The amount of malic acid is typically between about 0.19% to about 0.7% of the aqueous media; larger amounts tend to inhibit desired activity. Typically, the preferred nitrogen source is amino acids or peptides. The amino acids and peptides which are most preferred are those not produced by the L. oenos or Lactobacillus spp. being grown. Suitable essential minerals and vitamins for selected lactic acid bacteria are well known and need not be discussed here in detail. In the preferred cultures of the invention minerals and vitamins are provided, at least in part, by the yeast extract peptone and casein.

The culture media is typically inoculated with about $10^6$ to $10^7$ per liter of the bacteria to be grown. The culture medium, after growth, typically contains in excess of $10^9$ per liter of the desired bacteria.

The presently preferred media is a modified de Man, Rogosa, Sharpe media (MRSM) containing amounts of fructose within the scope of the invention, for example:

10 g/L Bacto peptone 8 g/L Casein hydrolysate 4 g/L Yeast extract 4 g/L DL-malate 5 g/L $KH_2PO_4$ 0.245 g/L $MgSO_4$ 0.2 g/L $MnSo_4 \times H_2O$ pH 4.5 adjusted with KOH add distilled water to 1 L While the present bacteria cultures are particularly adapted for malolactic fermentation of wines, they can also be employed in pickle manufacture and or silage, as have other similar bacteria.

EXAMPLES

Bacteria Used

The six Leuconostoc oenos strains used for these studies originated from different winegrowing regions of the world.

Some of these strains are well described and are part of commercial starter cultures, but also some experimental strains which have recently been described were included (Beelman et al., 1982, supra; Kunkee, 1974, supra; Lafon-Lafourcade et al., 1983, *Connaiss. Vigne. Vin.* 17:55–71; Henick-Kling et al., 1989, *Appl. Environ. Microbiol.* 55:2010–2016; Watson et al., 1985, in "Processing of the internat. symposium on cell climate vitic. and enol. OSU, Corvallis OR. p. 516–529; Krieger and Hammes, 1988, Der Deutsche Weinbau, 25–26:1152–1154). The strains and their origin are listed in Table 1. The cultures are maintained in the collection of the Department of Food Science, Cornell University, Geneva, N.Y.

nm greater than two). The modified Homohiochii medium (Krieger, 1989, supra) contained the following per liter: 10 g Bactopeptone (Difco Laboratories, Detroit, Mich.), 9 g yeast extract (Gibco Laboratories, Madison, Wis.), d5 g D-glucose (Fisher Scientific, Fair Lawn, N.J.), 5 g D-fructose (Sigma, St. Louis, Mo.), 5 g Na-acetate×3$H_2O$, 0.2 g $MgSO_4$×7$H_2O$, 0.05 g $MnSO_4$×4$H_2O$, 0.01 g $FeSO_4$×7$H_2O$ and 40 ml ethanol (abs.). The pH was adjusted to 5.4 with 5 N HCl. This culture was transferred 1:10 (v/v) in mod. Homohiochii medium and incubated for 48 h (final $OD_{650\ nm}$ greater than two). With this stock culture, the different starter culture media (500 ml lots in Pyrex bottles) were inoculated 1:25 (v/v). Table 2 shows the composition of the different culture media.

TABLE 2

COMPOSITION OF THE GROWTH MEDIA

| Components | | Mod. MRS Henick-Kling 1986 | M25/25 | M5/45 | Apple Juice media Krieger 1989 | HFCS42 | HFCS55 |
|---|---|---|---|---|---|---|---|
| Bactopeptone (Difco) | (g) | 10 | 10 | 10 | — | — | — |
| Casein hydrolysis (Gibco) | (g) | 8 | 8 | 8 | — | — | — |
| Yeast extract (Gibco) | (g) | 4 | 4 | 4 | 5 | 5 | 5 |
| DL-malate (Sigma) | (g) | 4 | 4 | 4 | — | 4 | 4 |
| $KH_2PO_4$ | (g) | 5 | 5 | 5 | — | — | — |
| $MgSO_4$ | (g) | 0.245 | 0.245 | 0.245 | 0.245 | 0.245 | 0.245 |
| $MnSO_4·XH_2O$ | (g) | 0.2 | 0.2 | 0.2 | 0.2 | 0.2 | 0.2 |
| Tween80 | (ml) | 1 | — | — | — | — | — |
| Vitamin Mixture | (mg) | N | N | N | Y | Y | Y |
| D-glucose (Fisher Sc) | (g) | 10 | 25 | 5 | — | — | — |
| D-fructose (Sigma) | (g) | 10 | 25 | 45 | 5 | — | — |
| Apple juice | (L) | — | — | — | 0.5[3] | — | — |
| High Fructose Corn Syrup | | | | | | | |
| IsoClear ™ 42 (Cargill)[1] | (L) | — | — | — | — | 0.5[3] | — |
| IsoClear ™ 55 (Cargill)[2] | (L) | — | — | — | — | — | 0.5[3] |
| pH | | 4.5 | 4.5 | 4.5 | 4.5 | 4.5 | 4.5 |
| Aqua dest. | | ad. 1 L | ad. 1 L | ad. 1 L | ad. 1 L | ad. 1 L | ad. 1 L |

[1] IsoClear ™ 42 (Cargill, Inc., Dayton, OH): 42% fructose, 55% glucose, 6% higher Saccharides, 36.7° Baume
[2] IsoClear ™ 55 (Cargill, Inc., Dayton, OH): 55% fructose, 41% glucose, 4% higher Saccharides, 40.0° Baume
[3] Sugar containing component was autoclaved separately

TABLE 1

ORIGIN OF *LEUCONOSTOC OENOS* STRAINS

| Strain | Origin | | Commercial culture | (Y/N) |
|---|---|---|---|---|
| Er-1a | Oregon wine | ATCC 3940 | Cornell University Geneva, USA | Y |
| Lo42 | Wurttemberg wine | — | University Hohenheim, FRG | Y |
| Lo107 | Wurttemberg wine | — | University Hohenheim, FRG | N |
| PSU-1 | Pennsylvania | — | Cornell University Geneva, USA | Y |
| Lc5m | Australian wine | — | Cornell University Geneva, USA | N |
| Oeno[R] | European wine | — | Microlife Technics Sarasota, USA | Y |

Preculture and Fermentation

Stock cultures were maintained at −85° C. Thawed cultures were transferred to a modified Homohiochii medium and incubated 3–5 days at 30° C. (final optical density at 650

Growth Rate and Dry Weight

Growth was followed by measuring the optical density (OD) at 650 nm. Twenty-four hours after reaching stationary phase, cells were harvested from 400 ml of culture by centrifugation at 9,000 g for 25 minutes, washed twice in 20 ml distilled water, centrifuged at 18,000 g for 20 minutes and the cell pellet was resuspended in 10 ml distilled water. For the calculation of the cell yield, the dry weight was determined, The washed cells were transferred into tared glass weighing bottles and dried at 105° C. to constant weight. The bottles were reweight at room temperature. The cell yield was calculated as g dry weight/l fermentation broth. The number of viable cells in the starter culture was determined by plating onto modified Homohiochii agar plates. The plates were incubated at 30° C. for 6–7 days.

MLF in Wine

With two strains (Er-1a and Lo107) studies were performed to determine the survival of the bacteria and malolactic activity in wine after growth in different starter culture media. A red and white wine were chosen for this test. Wine No. 1 was a 1989 Chardonnay from the Finger Lakes Region, New York State. The pH was 3.35, free $SO_2$ was 15 ppm, total $SO_2$ was 45 ppm alcohol 13 vol %. The $SO_2$ content was reduced with peroxide to a total $SO_2$ content of 10 mg/L. Wine No. 2 was a 1989 Cabernet Sauvignon (Finger Lakes Region, New York State ) pH 3.5 without SO$_2$. This wine already had undergone MLF. This fact resulted in a malic acid content of 0.25 g/L and a high lactic acid content of 7.05 g/L. Malic acid was readjusted to 2.9 g/L by the addition of L-malic acid (Sigma), the resulting pH was 3.30.

100 ml aliquotes of both wines were inoculated with the starter cultures at 0.1% (v/v). Malolactic fermentation was monitored by measuring the concentration of malic acid and lactic acid by HPLC (Tegmo-Larsson et al., 1989). The survival of the cultures was followed by the standard plating method using modified Homohiochii agar. Plates were incubated at 30° C. for 6–7 days. Fermentations were carried out in duplicate. The mean of duplicate sample analysis is reported.

Effect of the Different Culture Media on Growth and on Cell Yield of *Leuconostoc oenos* Cultures The data in Table 3a shows that there are large differences in the cell yield after fermentation in different media.

TABLE 3a

CELL YIELD OF *LEUCONOSTOC OENOS* STRAINS AFTER FERMENTATION IN DIFFERENT CULTURE MEDIA

| Strain | Culture media | | apple juice medium A | modified MRS- medium | M25/25 | M5/45 |
|---|---|---|---|---|---|---|
| | HF42 | HF55 | | | | |
| | Cell Yield (g dryweight/L culture media) | | | | | |
| Er-1a | 0.541 | 0.411 | 0.521 | 0.697 | 0.945 | 0.920 |
| Lo107 | 1.156 | 0.944 | 0.802 | 1.293 | 1.972 | 1.795 |
| Lo42 | 0.959 | 0.931 | 0.520 | 1.128 | 1.438 | 1.400 |
| PSU-1 | 0.418 | 0.411 | 0.725 | 0.590 | 1.005 | 1.000 |
| Lc5m | 0.590 | 0.693 | 0.695 | 0.703 | 1.623 | 1.210 |
| Oeno$^R$ | 0.666 | 0.486 | 0.628 | 0.846 | 1.238 | 0.525 |
| ave | 0.721 | 0.646 | 0.649 | 0.876 | 1.370 | 1.142 |
| s | 0.279 | 0.248 | 0.114 | 0.276 | 0.390 | 0.435 |

For all strains the cell yield was much larger after fermentation in a synthetic medium containing 25 g fructose and 25 g glucose (95% compared with AJM (paired T-test, signif. 0.003), or>95% compared with MRSM and HFCSs). With the exception of strain Oeno$^R$, a fermentation in a synthetic medium containing 5 g glucose and 45 g fructose gave similar high cell yields (90% to 95% higher compared with MRSM and HFCSs). The cell yields after fermentation in the traditionally used grape or apple juice media (AJM) ranged on average 50% (49.2±13.4) lower. Cells yields after fermentation in a modified MRS medium (Henick-Kling, 1986, *supra*) containing 10 g/L of each glucose and fructose also showed lower results. The high fructose corn syrup (HFCS) medium lacked a good buffering system. The pH after fermentation in HFCS42 and HFCS55 was on average 3.16 and 3.2, respectively. The pH after fermentation in the synthetic media ranged much higher: pH 3.66 in M25/25 and pH 3.72 in M5/45. The pH after fermentation in AJM with pH 3.59 was intermediate to the values in HFCS and M25/25 and M5/45. Presumably there was an inhibition of the bacterial growth caused by the low pH in the media. The experiment was repeated for Er-1a and Lo107. In this case, the apple juice in the AJM was replaced with a fresh apple juice from another lot. The cell yields for the AJM were higher in this case, however, the yields in the synthetic media were higher again. For Er-1a even the number of viable cells after cultivation in a synthetic media was about 80% higher. The influence on the rate of growth was not that obvious, on average the fermentation in M5/45 was finished 12 h earlier in comparison to all other fermentations.

TABLE 3b

CELL YIELD OF *LEUCONOSTOC OENOS* ER-1A AND LO107 AFTER FERMENTATION IN APPLE JUICE AND SYNTHETIC MEDIA

| Strain | Culture media apple juice medium B | M25/25 | M5/45 |
|---|---|---|---|
| | Cell Yield (g dryweight/L culture medium) | | |
| Er-1a | 0.650 | 0.795 | 0.681 |
| Lo107 | 1.264 | 1.792 | 1.548 |
| | Viable Cells After Fermentation (CFU/ml) | | |
| Er-1a | 4.65 × 10$^9$ | 1.2 × 10$^{10}$ | 1.15 × 10$^{10}$ |
| Lo107 | 2.11 × 10$^{10}$ | 2.14 × 10$^{10}$ | 1.65 × 10$^{10}$ |

Effect of Glucose and Fructose on Culture Growth

Figure 2:
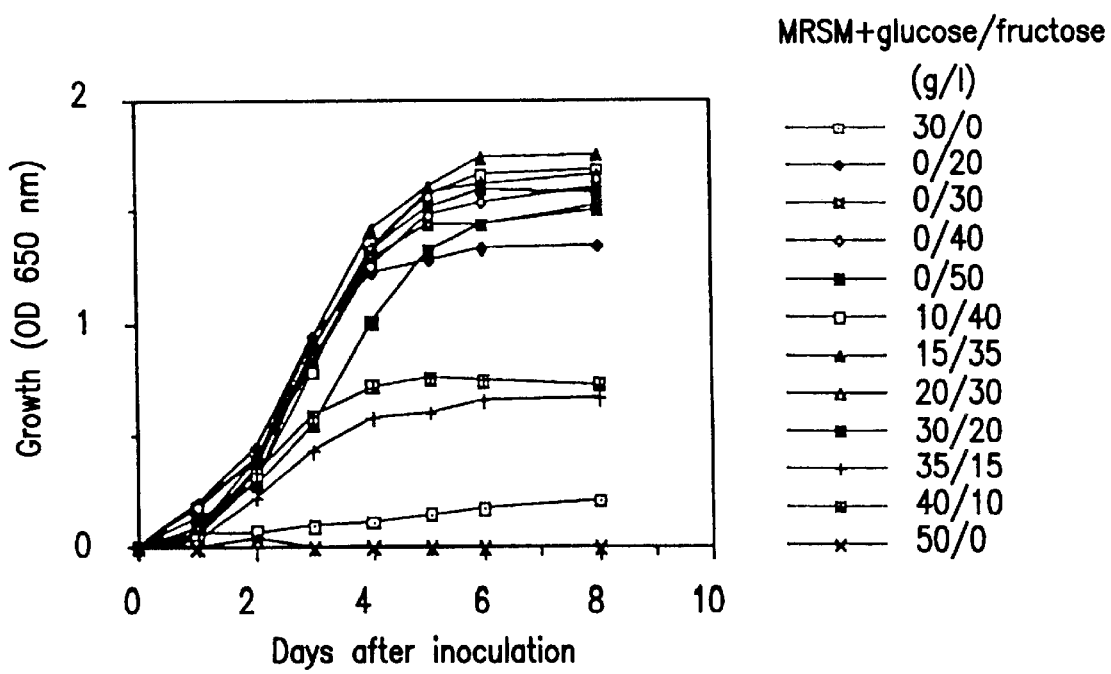
FIG. 2 shows growth of Leuconostoc oenos Er-1a in culture medium as a function of the glucose and fructose concentration in the medium.

Various combinations of glucose and fructose were compared in the MRSM medium (FIGS. 1 and 2). The data show that most rapid growth and highest cell density was obtained in media containing a minimum of 30 g/L fructose and a maximum fructose content of 45 g/L fructose (total fructose+glucose 50 g/L). No growth was obtained in media containing only glucose (30 to 50 g/L).

Figure 3:
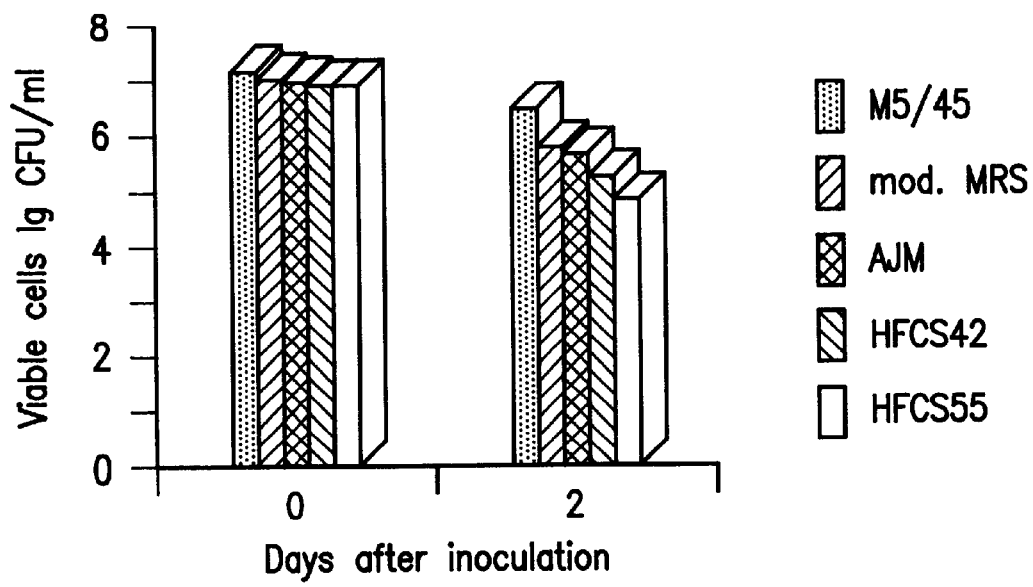
FIG. 3 shows the survival of Leuconostoc oenos Er-1a in a 1989 Chardonnay wine after growth in different culture media at 25° C.
Figure 4:
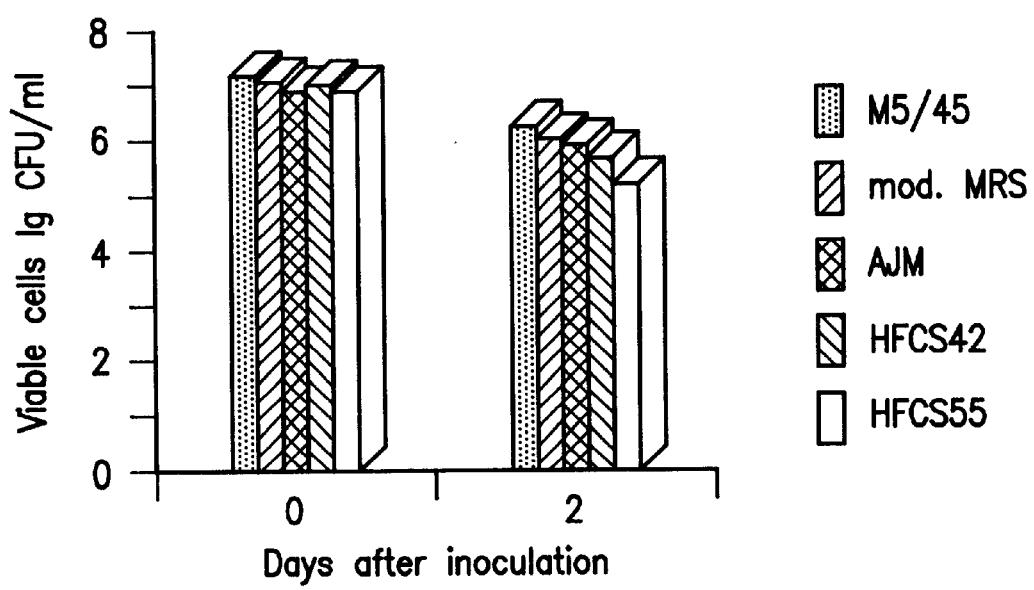
FIG. 4 shows the survival of leuconostoc oenos Lo107 in a 1989 Chardonnay wine after growth in a different culture media at 25° C.
Figure 5:
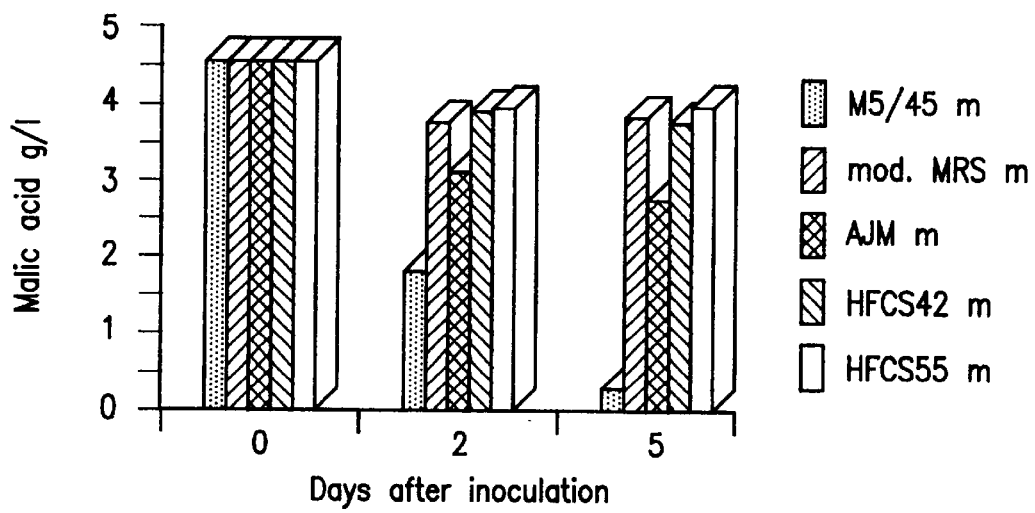
FIG. 5 shows malic acid degradation with Leuconostoc oenos Er-1a in a 1989 Chardonnay wine at 25° C.
Figure 6:
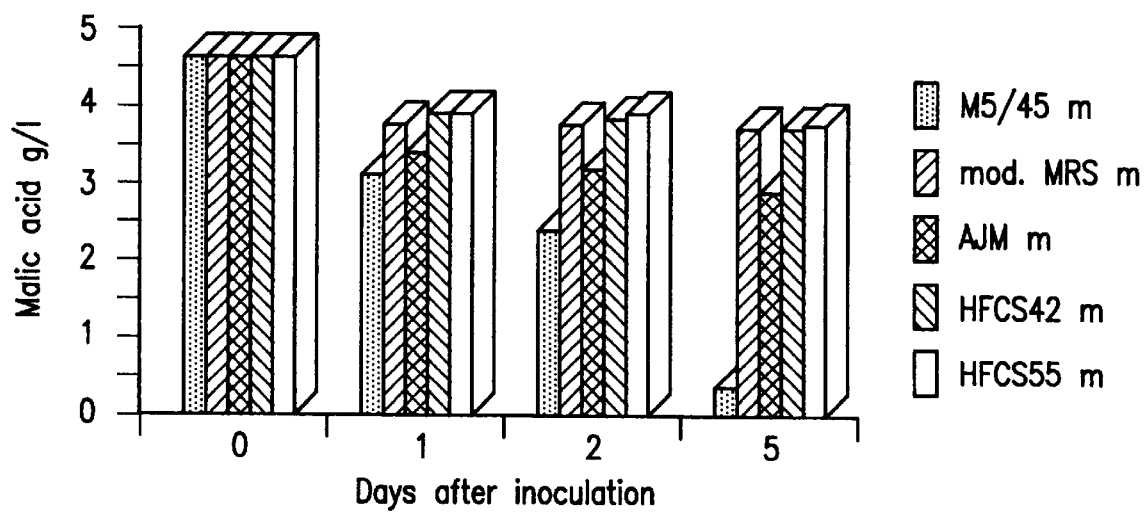
FIG. 6 shows malic acid degradation with Leuconostoc oenos Lo107 in a 1989 Chardonnay wine at 25° C.

Effect of the Growth in Different Culture Media on Survival and Malolactic Activity of the Strains in Wine Studies were performed to determine the ability of Er-1a and Lo107 after growth in different culture media to survive in a 1989 Chardonnay and a 1989 Cabernet Sauvignon and to degrade malic acid in these wines. FIGS. 3 and 4 show that the survival of Er-1a and Lo107 was better when they had been grown in the synthetic medium M5/45. The survival of the strain grown in MRSM and in apple juice media was about the same. A faster die-off was observed when the strains were grown in high fructose corn syrup HFCS55. The low pH in this medium at the end of fermentation likely caused some cell membrane damage, which had an influence on the survival of the bacteria in the Chardonnay wine. However same die-off was observed in all cultures. After seven days, the number of viable cells in all trials was below 100 CFU/ml. The die-off likely was due to some residual peroxide from the SO$_2$ removal. However, data in FIGS. 5 and 6 show that Er-1a as well as Lo107 fermented in M5/45 were highly active in this wine. Both strains finished malolactic fermentation in less than one week. Within five days, the initial malic acid content of 4.56 g/L was lowered to 0.31 g/L. In comparison both strains fermented in the MRSM in HFCS42 and in HFCS55 media didn't degrade more than an initial 1 g/L of malic acid. The bacteria grown in AJM degraded about 2 g/L malic acid during this experiment.

Figure 7:
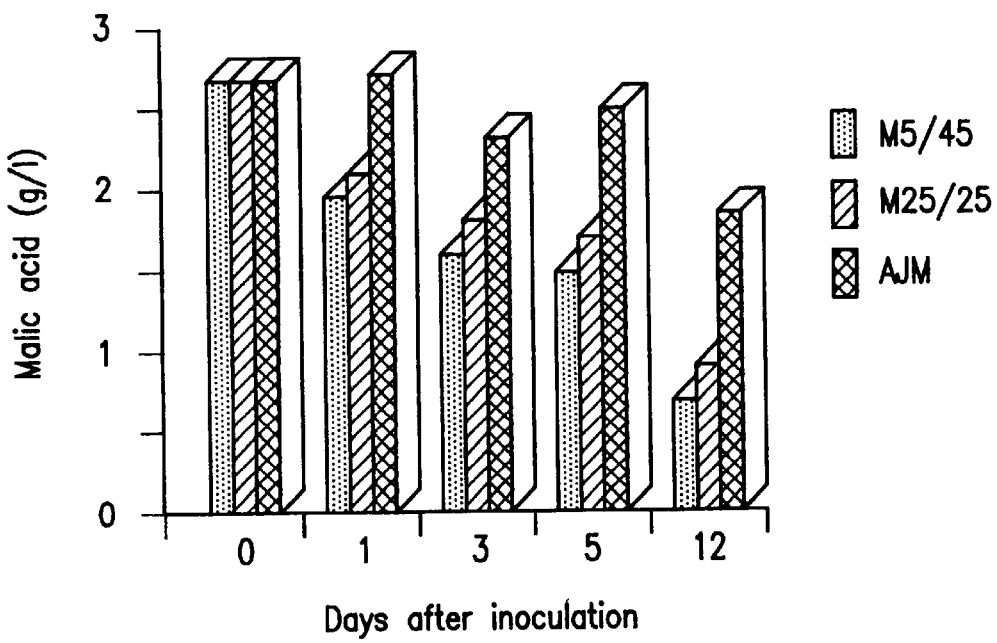
FIG. 7 shows malic acid degradation with Leuconostoc oenos Er-1a in a 1989 Cabernet Sauvignon wine at 25° C.
Figure 8:
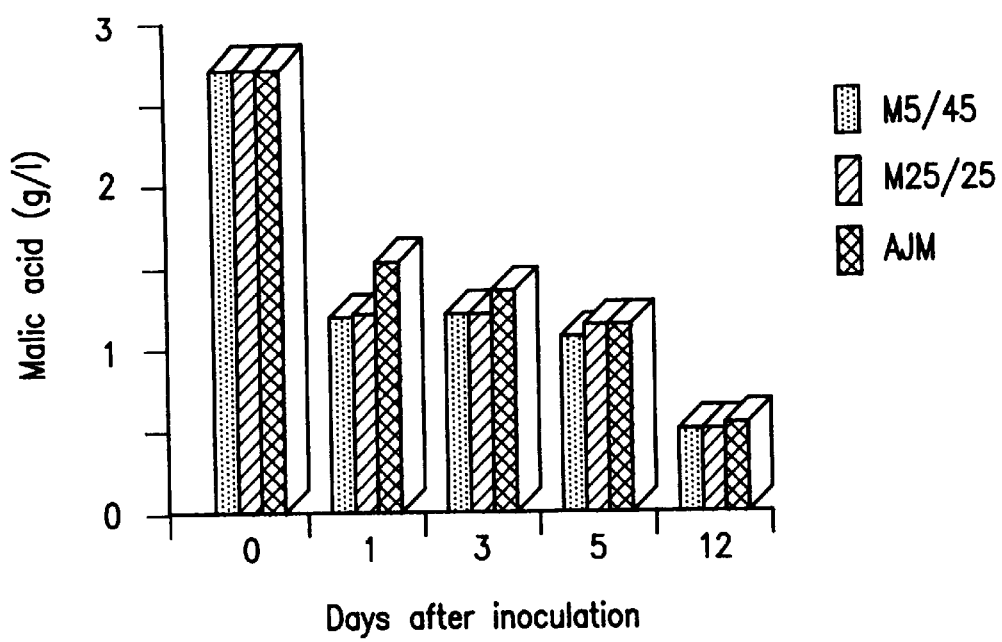
FIG. 8 shows malic acid degradation with Leuconostoc oenos Lo107 in a 1989 Cabernet Sauvignon wine at 25° C.

FIGS. 7 and 8 show the malic acid degradation with Er-1a and Lo107 in a 1989 Cabernet Sauvignon after growth in M5/45, M25/25, and in AJM. In all trials malic acid was degraded. While with Lo107 the differences between the different cultures were not that evident—the malic acid degradation with Lo107 fermented in M5/45 and M25/25 was somewhat faster than with Lo107 fermented in AJM— the differences with Er-1a fermented in the three culture media were large. In the 1989 Cabernet Sauvignon, Er-1a grown in M5/45 degraded malic acid from 2.8 g/L to 0.66 g/L in 12 days, when grown in M25/25 the malic acid content in the wine after 12 days was 0.9 g/L, and when grown in AJM it was 1.82 g/L. For all different fermentations the survival of both strains in the 1989 Cabernet Sauvignon was good.

TABLE 4a

TIME REQUIRED FOR *LEUCONOSTOC OENOS* STRAINS TO REACH MAXIMUM CELL DENSITY IN DIFFERENT CULTURE MEDIA

| | Culture media | | apple juice medium A | modified MRS-media | | |
|---|---|---|---|---|---|---|
| Strain | HF42 | HF55 | | | M25/25 | M5/45 |

Growth Time (h) Indicated by Maximum Optical Density (650 nm)

| | | | | | | |
|---|---|---|---|---|---|---|
| Er-1a | 42 | 90 | 90 | 42 | 64 | 64 |
| Lo107 | 48 | 48 | 48 | 56 | 48 | 48 |
| Lo42 | 60 | 72 | 84 | 42 | 42 | 42 |
| PSU-1 | 64 | 96 | 64 | 96 | 96 | 64 |
| Lc5m | 64 | 48 | 48 | 60 | 60 | 40 |
| Oeno | 60 | 60 | 42 | 60 | 60 | 42 |

TABLE 4b

TIME REQUIRED FOR *LEUCONOSTOC OENOS* ER-1A and LO107 TO REACH MAXIMUM CELL DENSITY IN DIFFERENT CULTURE MEDIA

| Strain | Culture media apple juice medium B | M25/25 | M5/45 |
|---|---|---|---|

Growth Time (h) Indicated by Maximum Optical Density (650 nm)

| | | | |
|---|---|---|---|
| Er-1a | 84 | 72 | 72 |
| Lo107 | 84 | 60 | 72 |

The data reported show the influence of the culture media on the cell yield and the malolactic activity in wine. The fermentation of *Leuconostoc oenos* strains in synthetic media M25/24 and M5/45 resulted in larger cell yields and the malolactic activity of the strains fermented in M5/45 was much higher. Another advantage of a synthetic medium in comparison with a medium based on grape or apple juice is the better definition and standardization of this media. Grape and apple juices show large variations in their composition, which also might influence the growth rate and the cell yield. Comparison of Cell Yield (Mass) From Different Media
USE OF FRUCTOSE IN GROWTH MEDIUM FOR *Leuconostoc oenos*
Medium: MRSM (Modified deMan, Rogosa, Sharpe medium)
10 g/L Bacto peptone
8 g/L Casein hydrolysate
4 g/L Yeast extract
4 g/L DL-malate
1 ml/L Tween 80
5 g/L KH2PO4
0.245 g/L MgSO4
0.2 g/L MnSO4×H2O
pH 4.5 with KOH
aqua dest. ad. 1 L

| Autoclave 15 minutes (121° C., 15 psi). | |
|---|---|
| M 10/10 | 10 g/L glucose + 10 g/L fructose + MRSM |
| M 25/25 | 25 g/L glucose + 25 g/L fructose + MRSM |
| M 5/45 | 5 g/L glucose _ 45 g/L fructose + MRSM |

Apple Juice Media (AJM)
  apple juice water 1:1
  5 g/L yeast extract
  0.245 g/L MgSO4
  0.2 g/L MnSO4×H2O
  vitamins
  pH 4.5 with KOH
High Fructose Corn Syrup (HFCS)
  42% and 55%
  HFCS: water 1:1
  5 g/L yeast extract
  0.245 g/L MgSO4
  0.2 g/L MnSO4×H2O
  vitamins
  pH 4.5 with KOH
Bacteria: PSU-1, Lo42, Lo107, Er-1a, Lc5m, Microlife OENO$^R$
  growth in 0.5 L duplicate batches
  determine growth rate (OD 650) 12,24,36,48,60,72 . . . h
  final cell mass (400 ml) 24 h at 105° C.
MLF in wine:
  cell counts after harvest=inoculation rate
  cell counts after 24h and after 48h (96h)
repetition with Lo107 and Er-1a

TABLE 5

COMPARISON OF CELL YIELD (MASS) FROM DIFFERENT MEDIA

| media | φ cell yield | (g dryweight/L) | paired T-test | significant % |
|---|---|---|---|---|
| AJM - MRSM | 0.649 | 0.876 | 0.105 | 90% |
| AJM - M25/25 | 0.649 | 1.370 | 0.003 | 95% |
| AJM - M5/45 | 0.649 | 1.142 | 0.03 | 95% |
| M25/25 - M5/45 | 1.370 | 1.142 | 0.104 | 90% |
| AJM - HFCS42 | 0.649 | 0.722 | 0.551 | no diff |
| AJM - HFCS55 | 0.649 | 0.646 | 0.982 | no diff |
| MRSM - M25/25 | 0.876 | 1.370 | 0.005 | >95% |
| MRSM - M5/45 | 0.876 | 1.142 | 0.090 | 91% |
| HFCS42-HFCS55 | 0.722 | 0.646 | 0.181 | 82% |
| HFCS42-M25/25 | 0.722 | 1.370 | 0.001 | >95% |
| HFCS42 - M5/45 | 0.722 | 1.142 | 0.017 | >95% |

We claim:

1. A culture medium for a starter culture for winemaking involving malolactic fermentation, said culture medium being a synthetic non-vegetable juice containing medium comprising on an aqueous liquid medium basis:
   (a) from about 4 to about 6% of a sole carbohydrate source consisting essentially of fructose and glucose and containing on a fructose plus glucose basis from about 97% to about 55% fructose and from about 3% to about 45% glucose,
   (b) from about 0.19% to about 0.7% L-malic acid or salt thereof,
   (c) malolactic bacteria growth supporting amount of a nitrogen source,
   (d) malolactic bacteria growth supporting amount of essential minerals and vitamins.

2. A method of propagating *Leuconostoc oenos* strains selected from the group consisting of Er-1a, Lo107, Lo42, PSU-1, Lc5m and Oeno, said method comprising propagating said bacteria in a culture medium which consists essentially of the culture medium of claim 1.

3. The culture medium of claim 1 which contains a buffer which keeps the pH obtained on completion of fermentation above 3.6.

4. The culture medium of claim 1 where the percent of glucose in the sole carbohydrate source on a fructose plus glucose basis is between about 5% and 20%.

5. The culture medium of claim 1 wherein the source of L-malic acid or salt thereof is malate and wherein sources of nitrogen, essential minerals and vitamins are peptides, casein hydrolysate, yeast extract, $KH_2PO_4$, magnesium salt and manganese salt.

6. The culture medium of claim 1 wherein the nitrogen source is present in a *Leuconostoc oenos* growth supporting amount and the essential minerals and vitamins are present in a *Leuconostoc oenos* growth supporting amount.

7. The culture medium of claim 6 wherein the source of L-malic acid or salt thereof is malate and wherein sources of nitrogen, essential minerals and vitamins are peptides, casein hydrolysate, yeast extract, $KH_2PO_4$, magnesium salt and manganese salt.

8. The culture medium of claim 7 wherein said sole carbohydrate source is present in an amount of 5% on an aqueous liquid medium basis.

9. The culture medium of claim 8 which contains 10 g/l bactopeptone, 8 g/l casein hydrolysate, 4 g/l yeast extract, 4 g/l DL-malate, 5 g/l $KH_2PO_4$, 0.245 g/l $MgSO_4$ and 0.2 g/l $MnSO_4$ X $H_2O$ in addition to said carbohydrate source.

10. A culture medium for a starter culture for winemaking involving malolactic fermentation, said culture medium being a synthetic non-vegetable juice containing medium comprising on an aqueous liquid medium basis:

(a) from about 4 to about 6% of a sole carbohydrate source consisting essentially of fructose and glucose and containing on a fructose plus glucose basis from about 97% to about 50% fructose and from about 3% to about 50% glucose, (b) from about 0.19% to about 0.7% L-malic acid or salt thereof, (c) malolactic bacteria growth supporting amount of a nitrogen source, (d) malolactic bacteria growth supporting amount of essential minerals and vitamins.

11. The culture medium of claim 10 wherein the nitrogen source is present in a *Leuconostoc oenos* growth supporting amount and the essential minerals and vitamins are present in a *Leuconostoc oenos* growth supporting amount.

12. The culture medium of claim 11 wherein the source of L-malic acid or salt thereof is malate and wherein sources of nitrogen, essential minerals and vitamins are peptides, casein hydrolysate, yeast extract, $KH_2PO_4$, magnesium salt and manganese salt.

13. The culture medium of claim 12 wherein said sole carbohydrate source is present in an amount of 5% on an aqueous liquid medium basis.

14. The culture medium of claim 13 which contains 10 g/l bactopeptone, 8 g/l casein hydrolysate, 4 g/l yeast extract, 4 g/l DL-malate, 5 g/l $KH_2PO_4$, 0.245 g/l $MgSO_4$ and 0.2 g/l $MnSO_4$ X $H_2O$ in addition to said carbohydrate source.

15. A culture medium for a starter culture for winemaking involving malolactic fermentation, said culture medium being a synthetic non-vegetable juice containing medium comprising on an aqueous liquid medium basis:

(a) from about 30 g/L to about 60 g/L of a sole carbohydrate source consisting essentially of fructose and glucose and including glucose in an amount providing at least 5 g/L of glucose and including fructose in an amount proving at least 15 g/L of fructose;

(b) from about 0.19% to about 0.7% L-malic acid or salt thereof, (c) malolactic bacteria growth supporting amount of a nitrogen source, (d) malolactic bacteria growth supporting amount of essential minerals and vitamins.

16. The culture medium of claim 15 wherein the nitrogen source is present in a *Leuconostoc oenos* growth supporting amount and the essential minerals and vitamins are present in a *Leuconostoc oenos* growth supporting amount.

17. The culture medium of claim 16 wherein the source of L-malic acid or salt thereof is malate and wherein sources of nitrogen, essential minerals and vitamins are peptides, casein hydrolysate, yeast extract, $KH_2PO_4$, magnesium slat and manganese salt.

18. The culture medium of claim 17 which contains 10 g/L bactopeptone, 8 g/L casein hydrolysate, 4 g/L yeast extract, 4 g/L DL-malate, 5 g/L $KH_2PO_4$, 0.245 g/L $MgSO_4$ and 0.2 g/L $MnSO_4$ X $H_2O$ in addition to said carbohydrate source.

* * * * *